United States Patent [19]
Medenica et al.

[11] Patent Number: 5,744,585
[45] Date of Patent: Apr. 28, 1998

[54] HUMAN MONOCLONAL ANTIBODY AGAINST LUNG CARCINOMA

[76] Inventors: Rajko D. Medenica, Once Ocean Point, Port Royal Plantation, Hilton Head Island, S.C. 29928; Sonjoy Mukerjee, 40 Bill Fries Dr., Apt. H5, Hilton Head Island, S.C. 29926

[21] Appl. No.: 405,034

[22] Filed: Mar. 16, 1995

[51] Int. Cl.$^6$ .................. C07K 16/30; G01N 33/574; G01N 33/577

[52] U.S. Cl. .................. 530/388.15; 530/388.8; 435/7.23; 435/7.24; 435/7.95

[58] Field of Search .................. 530/388.1, 388.15, 530/388.8, 388.85; 435/172.2, 240.27; 424/141.1, 142.1, 155.1, 156.1

[56] References Cited

U.S. PATENT DOCUMENTS

| | | |
|---|---|---|
| 4,585,742 | 4/1986 | Bernal . |
| 4,800,155 | 1/1989 | Taniguchi et al. . |
| 5,006,470 | 4/1991 | Yamaguchi et al. . |
| 5,134,075 | 7/1992 | Hellstrom et al. . |
| 5,227,471 | 7/1993 | Wright, Jr. . |
| 5,242,824 | 9/1993 | Hellstrom et al. . |
| 5,338,661 | 8/1994 | Jensenius et al. . |
| 5,348,880 | 9/1994 | Hanna . |

OTHER PUBLICATIONS

Kusakabe, J. Nuclear Medicine, Feb. 1994 35:289–295.
Souhani, The Lancet, Aug. 8, 1987 pp. 325–326.
Illustrated Dictionary of Immunology, Cruse & Lewis, p. 107, 1995, CRC Press.
Derbyshire et al, Br. J. Cancer 67:1242–1247 (1993).
Cronin, Cancer Research 42:292–300, 1982.
Moore, Clin. Chem. 3519:1849–1853, 1989.
Souhani et al. JNCI 83:609–612, 1991.
Bhattacharya-Chatterjee, M. et al., 1990, "Murine Monoclonal Anti-idiotype Antibody as a Potential Network Antigen for Human Carcinoembryonic Antigen," J. of Immun., 145:2758–2765.
Brezicka, F.T. et al., 1991, "Tumor–Cell Killing by MAbs Against Fucosyl GM1, a Ganglioside Antigen Associated with Small–cell Lung Carcinoma," Int. J. Cancer, 49:911–918.
Caamano, J. et al., 1991, "Detection of p53 in Primary Lung Tumors and Nonsmall Cell Lung Carcinoma Cell Lines," Amer. J. Pathology, 139:839–845.
Chang, H.R. et al., 1994, "Tumor Associated Antigens Recognized by Human Monoclonal Antibodies," Ann. Surg. Oncol., 1(3):213–221.
Deng-Shun, W. et al., "Detection of Antigens Associated with Lung Carcinoma in Sera by Monoclonal Antibodies WLA-2C4 and C1-3," Chinese Med. J., 105:905–908.
Denton, G.W.L., et al., 1994, "Clinical Outcome of Colorectal Cancer Patients Treated with Human Monoclonal Anti-Idiotypic Antibody," Int. J. Cancer, 57:10–14.
Ey, P.L. et al., 1978, "Isolation of Pure IgG$_{1a}$, IgG$_{2a}$ and IgG$_{2b}$ Immunoglobulins from Mouse Using Protein A–Sepharose," Immunochemistry, 15:429–436.

Henderson, E. et al., 1977, "Efficiency of Transformation of Lymphocytes by EBV," Virology, 76:152–163.
Katsuki, T. et al., 1977, "Identification of the Target Cells in Human B Lymphocytes for Transformation by EBV," Virology, 83:287–294.
Lehmann, H.P. et al., 1992, "Tumor–Antigen–Specific Humoral Immune Response of Animals to Anti–Idiotypic Antibodies and Comparative Serological Analysis of Patients with Small–Cell Lung Carcinoma," Int. J. Cancer, 50:86–92.
Medcalf, E.A. et al., 1992, "Temperature–sensitive Mutants of p53 Associated with Human Carcinoma of the Lung," Oncogene, 7:71–76.
Moss, F. et al., 1991, "Differential Expression of Antigens by Human Small Cell Lunh Carcinoma in Sections of Tumour and in Serous Effusions," Br. J. Cancer, 63:54–55.
Niklinski J. et al., 1992, "Evaluation of Squamous Cell Carcinoma Antigen (SCC–Ag) in the Diagnosis and Follow–up of Patients with Non–small Cell Lung Carcinoma," Neoplasma, 39:279–282.
Pezzella, F., et al., 1993, "bcl–2 Protein in Non–small–cell Lung Carcinoma," NE J. of Medicine, 329:690–694.
Sanger, F. et al., 1977, "DNA Sequencing With Chain–terminating Inhibitors," PNAS, USA, 74:5463–5467.
Shijubo, N. et al., 1992, "Granulocyte Colony–Stimulating Factor–Producing Large Cell Undifferentiated Carcinoma of the Lung," Internal Medicine, 31:277–280).1.
Skov, B.G. et al., 1991, "Expression of 'small cell carcinoma antigens' in Primary Small Cell Lunh Cancer and Metastases: an Immunohistochemical Study," Br. J. Cancer 63: 46–48.
Speirs, V. et al., 1993, "Localization of MOC–1 Cell Surface Antigen in Small–dell Lung Carcinoma Cell Lines: An Immunohistochemical and Immunoelectron Microscopic Study," J. Histochemistry & Cytochemistry, 41:1303–1310.
Stastny, J.J., et al., 1991, "Monoclonal Antibody Identification and Characterization of Two Human Sarcoma–associated Antigens," Cancer Research, 51:3768–3773.
Stephenson, J.R., et al., 1984, "Production and Purification of Murine Monoclonal Antibodies; Aberrant Elution from Protein A Sepharose CL–4b," Anal. Biochem., 142:189–195.
Underwood, P.A. et al, 1983, "Use of Protein A to Remove Immunoglobulins from Serum in Hybridoma Culture Media," J. Immunol. Methods, 60:33–45.
Waibel, R., et al., 1991, "Monoclonal Antibodies Defining the Cluster–5A Small Cell Lung Carcinoma Antigen," Br. J. Cancer, 63:29–32.
Yakose, T. et al., 1991, "Immunohistochemical and Ultrastructural Study of Mixed Small cell/Large cell Carcinoma of the Lung," Acta Pathol Jpn, 41:540–551.
Zwicky, C. et al., 1991, "Polyclonal Anti–idiotypic Antibodies Mimicking the Small Cell Lung Carcinoma Antigen Cluster 5A Interact with a Panel of Antibodies and Induce Specific Immune Response in Animals," Br. J. Cancer, 63:67–70.

Primary Examiner—Marian C. Knode
Assistant Examiner—Nancy A. Johnson
Attorney, Agent, or Firm—DeWitt Ross & Stevens SC

[57] ABSTRACT

A human monoclonal antibody TB2A36C3 which shows high specificity against lung tumor antigens is described. TB2A36C3 can be used clinically for immunotherapy.

11 Claims, 13 Drawing Sheets

| QUAD | EVENTS | % GATED | % TOTAL | X MEAN | Y MEAN |
|---|---|---|---|---|---|
| UL | 9.0 | 0.34 | 0.09 | 34.56 | 115.11 |
| UR | 17.0 | 0.64 | 0.17 | 137.59 | 112.76 |
| LL | 1691 | 63.91 | 16.91 | 29.57 | 29.20 |
| LR | 929 | 35.11 | 9.29 | 160.18 | 17.71 |

| QUAD | EVENTS | % GATED | % TOTAL | X MEAN | Y MEAN |
|---|---|---|---|---|---|
| UL | 966.0 | 57.67 | 19.32 | 28.96 | 145.80 |
| UR | 531.0 | 31.70 | 10.62 | 148.17 | 134.70 |
| LL | 73.0 | 4.36 | 1.46 | 35.19 | 39.88 |
| LR | 105.0 | 6.27 | 2.10 | 126.80 | 26.47 |

| QUAD | EVENTS | % GATED | % TOTAL | X MEAN | Y MEAN |
|------|--------|---------|---------|--------|--------|
| UL | 85.0 | 1.81 | 1.70 | 36.32 | 116.48 |
| UR | 96.0 | 2.04 | 1.92 | 132.43 | 113.65 |
| LL | 2995 | 63.70 | 59.90 | 32.09 | 12.36 |
| LR | 1526 | 32.45 | 30.52 | 159.93 | 12.20 |

| QUAD | EVENTS | % GATED | % TOTAL | X MEAN | Y MEAN |
|------|--------|---------|---------|--------|--------|
| UL | 131.0 | 2.78 | 2.62 | 34.98 | 115.49 |
| UR | 113.0 | 2.40 | 2.26 | 144.77 | 115.03 |
| LL | 2993 | 63.49 | 59.86 | 31.82 | 12.70 |
| LR | 1477 | 31.33 | 29.54 | 160.22 | 12.69 |

| QUAD | EVENTS | % GATED | % TOTAL | X MEAN | Y MEAN |
|---|---|---|---|---|---|
| UL | 12.0 | 0.60 | 0.12 | 34.67 | 106.0 |
| UR | 2.0 | 0.10 | 0.02 | 116.0 | 108.5 |
| LL | 771 | 38.43 | 7.71 | 34.49 | 27.30 |
| LR | 1221 | 60.87 | 12.21 | 121.70 | 27.56 |

| QUAD | EVENTS | % GATED | % TOTAL | X MEAN | Y MEAN |
|---|---|---|---|---|---|
| UL | 214.0 | 36.2 | 2.14 | 32.34 | 144.7 |
| UR | 333.0 | 56.3 | 3.33 | 136.6 | 151.4 |
| LL | 38.0 | 6.43 | 0.38 | 32.26 | 39.05 |
| LR | 6.0 | 1.02 | 0.06 | 145.67 | 36.17 |

| QUAD | EVENTS | % GATED | % TOTAL | X MEAN | Y MEAN |
|------|--------|---------|---------|--------|--------|
| UL | 204.0 | 4.57 | 4.08 | 35.23 | 112.83 |
| UR | 54.0 | 1.21 | 1.08 | 135.69 | 113.48 |
| LL | 1525 | 34.17 | 30.50 | 34.44 | 22.82 |
| LR | 2680 | 60.05 | 53.60 | 137.78 | 12.03 |

| QUAD | EVENTS | % GATED | % TOTAL | X MEAN | Y MEAN |
|------|--------|---------|---------|--------|--------|
| UL | 139.0 | 3.01 | 2.78 | 34.83 | 112.3 |
| UR | 53.0 | 1.15 | 1.06 | 141.7 | 106.5 |
| LL | 1656 | 35.88 | 33.12 | 35.52 | 22.09 |
| LR | 2768 | 59.97 | 53.36 | 140.89 | 10.49 |

| LEFT | RIGHT | EVENTS | % GATED | % TOTAL |
|---|---|---|---|---|
| 2.06 | 53.15 | 879 | 44.0 | 44.0 |
| 55.10 | 8347.73 | 1101 | 55.0 | 55.0 |

| LEFT | RIGHT | EVENTS | % GATED | % TOTAL |
|---|---|---|---|---|
| 2.06 | 53.15 | 771.0 | 38.6 | 38.6 |
| 55.10 | 8347.73 | 1170 | 58.5 | 58.5 |

| LEFT | RIGHT | EVENTS | % GATED | % TOTAL |
|------|-------|--------|---------|---------|
| 2.06 | 53.15 | 887.0 | 44.0 | 44.4 |
| 55.10 | 8347.73 | 985.0 | 49.2 | 49.2 |

| LEFT | RIGHT | EVENTS | % GATED | % TOTAL |
|------|-------|--------|---------|---------|
| 1.66 | 373.72 | 867.0 | 43.3 | 43.3 |
| 387.47 | 10000 | 1130 | 56.5 | 56.5 |

| LEFT | RIGHT | EVENTS | % GATED | % TOTAL |
|---|---|---|---|---|
| 1.66 | 373.72 | 647.0 | 32.4 | 32.4 |
| 387.47 | 10000 | 1352 | 67.6 | 67.6 |

| LEFT | RIGHT | EVENTS | % GATED | % TOTAL |
|---|---|---|---|---|
| 3.41 | 88.12 | 1739 | 87.0 | 87.0 |
| 91.37 | 10000 | 260.0 | 13.0 | 13.0 |

| LEFT | RIGHT | EVENTS | % GATED | % TOTAL |
|---|---|---|---|---|
| 3.41 | 88.12 | 1473 | 73.7 | 73.7 |
| 91.37 | 10000 | 525.0 | 26.3 | 26.3 |

| LEFT | RIGHT | EVENTS | % GATED | % TOTAL |
|---|---|---|---|---|
| 3.41 | 88.12 | 1456 | 72.8 | 72.8 |
| 91.37 | 10000 | 541.0 | 27.1 | 27.1 |

```
ATG GAA ACC CCA GCG CAG CTT CTC TTC CTC
Met Glu Thr Pro Ala Gln Leu Leu Phe Leu    10

CTG CTA CTC TGG CTC CCA GAT ACC ACC GGA
Leu Leu Leu Trp Leu Pro Asp Thr Thr Gly    20

GAA ATT GTG TTG ACG CAG TCT CCA GGT ACC
Glu Ile Val Leu Thr Gln Ser Pro Gly Thr    30

CTG TCT TTG TCT CCA GGG GAA AGA GCC ACC
Leu Ser Leu Ser Pro Gly Glu Arg Ala Thr    40

CTC TCC TGC AGG GCC AGT CAG AGT TTT AGC
Leu Ser Cys Arg Ala Ser Gln Ser Phe Ser    50

AGA AGC TTC TTA GCC TGG TAC CAG CAG AAA
Arg Ser Phe Leu Ala Trp Tyr Gln Gln Lys    60

CCT GGC CAG GCT CCC AGC CTC CTC ATC TAT
Pro Gly Gln Ala Pro Ser Leu Leu Ile Tyr    70

GGT GCA TCC ACC AGG GCT ACT GGC ATC CCA
Gly Ala Ser Thr Arg Ala Thr Gly Ile Pro    80

GAC AGG TTC AGT GGC AGT GGG TCT GGG ACA
Asp Arg Phe Ser Gly Ser Gly Ser Gly Thr    90

GAC TTC ATT CTC ACC ATC AGC AGA CTG GAG
Asp Phe Ile Leu Thr Ile Ser Arg Leu Glu    100

CCT GAA GAT TTT GCA GTG TAT TAC TGT CAG
Pro Glu Asp Phe Ala Val Tyr Tyr Cys Gln    110

CAG TAT GGT AGC TCA GCT CGG TAC ACT TTT
Gln Tyr Gly Ser Ser Ala Arg Tyr Thr Phe    120

GGC CAG GGG ACC AAG CTG GAG ATC AAA CGA
Gly Gln Gly Thr Lys Leu Glu Ile Lys Arg    130

ACT GTG GCT GCA
Thr Val Ala Ala    134    (Seq. Id. No: 3)
```

HUMAN MONOCLONAL ANTIBODY AGAINST LUNG CARCINOMA

FIELD OF THE INVENTION

The present invention is generally directed to the fields of medicine and pharmacology, and specifically directed to a human monoclonal antibody which can be used as a therapy and a diagnostic procedure against cancer, specifically lung cancer.

REFERENCE TO CITATIONS

A full bibliographic citation of the references cited in this application can be found in the section preceding the nucleotide sequence listings.

DESCRIPTION OF PRIOR ART

Monoclonal antibodies against tumor-associated antigens are important to the detection of cancer because they are more specific than other conventional diagnostic methods. One problem, though, is that most of the monoclonal antibodies raised against cancer-associated antigens are of mouse origin, and are expressed by hybridomas resulting from a fusion of spleen cells from a mouse immunized with a human cancer cell line or cells from a cancer patient with a mouse myeloma cell line. Immunogenicity in the mouse is a requirement for antigens recognized by murine monoclonal antibodies and they do not necessarily correspond to antigens recognized by human antibodies. In addition, the therapeutic value of these murine monoclonal antibodies may be limited since patients recognize these antibodies as foreign proteins and may therefore develop an adverse immune response against the murine antibody. The result may be a neutralization of the therapeutic effect and triggering of potentially dangerous allergic reactions.

Human hybridoma antibodies may be more promising as diagnostic and therapeutic agents for administration to patients with cancer under the assumption that human monoclonal antibodies are less immunogenic in humans than heterologous antibodies and are capable of recognizing the relevant antigens.

Lung cancer is the most common lethal cancer in the United States. In 1992, 168,000 new cases and 146,000 deaths from lung cancer were estimated. The overall five-year survival rate for newly diagnosed cases of non-small cell lung cancer (NSCLC) is only 10–15%.

Thus, there exists a need for a human monoclonal antibody which can be used for diagnostic and therapeutic purposes relating to lung cancer.

SUMMARY OF THE INVENTION

The present invention derives from the development of a human monoclonal antibody, TB2A36C3, which is directed to improving methods of prevention, early detection and treatment of lung cancer. The human monoclonal antibody designated herein as TB2A36C3 is produced by a transformed human B-cell hybridoma immortalized by Epstein-Barr virus which was deposited under the terms of the Budapest Treaty with the American Type Culture Collection (12301 Parklawn Drive, Rockville, Md. 20852, USA) on 19 Jun. 1996 and given Accession No. CRL-12142.

The present invention is directed to a monoclonal antibody TB2A36C3 with high specificity against lung tumor antigens, produced by an Epstein-Barr Virus (EBV)-transformed human B-cell line TB94.

The present invention is more specifically directed to a human monoclonal antibody which shows positive reactivity against non-small cell lung cancer and small cell lung cancer and which shows no reactivity against breast, ovary, melanoma, leiomyosarcoma and leukemia/lymphoma cell lines.

The present invention is also directed to transformed human B-cell line immortalized by EBV.

The present invention is further directed to a monoclonal antibody which specifically binds to a 32 kD molecular weight antigen on NCIH69 cell line and a cluster of antigens from 28 kD to 106 kD in the NSCLC cell line NCIH661. Cell lines NCIH69 and NCIH661 are on deposit with the American Type Culture Collection under Accession No. ATCC HTB-119 and ATCC HTB-183, respectively.

The present invention is also directed to a monoclonal antibody TB2A36C3 with high specificity against lung tumor antigens, produced by an EBV transformed B-cell line TB94.

The present invention is also directed to a method of screening a sample of a body fluid or tissue for the presence of a carcinoma-associated antigen which comprises contacting a sample of a body fluid or tissue with the monoclonal antibody described above and detecting the binding of the antibody to the antigen present in the sample.

The present invention is further directed to a diagnostic aid for non-small cell lung cancer or small cell lung cancer, the diagnostic aid comprising the monoclonal antibody described above and a carrier.

The present invention is also directed to a method for activating immune competent cells CD4 or CD8 in a patient's blood system comprising exposing the blood system with an activating amount of the antibody described above.

The present invention is also directed to a bioreagent for antibody assays comprising a substantially pure peptide fragment F(ab')$_2$ of the monoclonal antibody TB2A36C3.

Further, the present invention is directed to a monoclonal antibody TB2A36C3 wherein the sequence of the light chain is illustrated in FIG. 10 [SEQ. ID. NO. 3].

There are several advantages of human monoclonal antibodies over conventional murine fusion products. For example, human immunoglobulin is far less immunogenic in humans than xenogenic mouse immunoglobulin. Further, auto-antibodies or naturally occurring human antibodies could be used as antigens to select and develop human monoclonal anti-idiotypic antibodies, which would potentially be useful for suppressing the response to auto-antigens or transplant antigens. The human immune response would generate a wider range of antibodies against human leukocyte antigen (HLA) and other polymorphic surface determinants than immunization across species barriers. Human monoclonal antibodies would tell us more than murine monoclonal antibodies about the spectrum of the human B-cell specificity repertoire. However, the difficulties encountered in the murine hybridoma field are relevant to the human system as well.

The present invention represents a considerable advance in the development of new medication against cancer. Because there is less risk of sensitization, human monoclonal antibodies are preferable over mouse monoclonal antibodies for therapy of human diseases.

The antibody, being highly specific, can be administered clinically and can show tumor lysis. It can also be conjugated to a radioactive compound for radioimmunotherapy. Additionally, in combination with standard chemotherapeutic agents, the antibody will demonstrate effective lysis of tumors.

In an in-vitro analysis, the antibody can be used as a method of screening for circulating tumor antigens in patients' sera. Also, in a point biopsy or after surgery, tissue sections can be stained with the antibody to detect the presence of the carcinoma-associated antigens.

Localization of the tumor can be screened by immunoscintigraphy when the antibody conjugated with a radioactive compound is injected in-vivo inside a lung tumor-bearing person.

Other objects and advantages of the invention will be apparent from the following detailed description and figures setting forth the preferred embodiment of the invention.

DESCRIPTION OF THE DRAWINGS

FIG. 10 is a nucleotide sequence of the light chain of the TB2A36C3 monoclonal antibody [SEQ. ID. NO. 3].

DETAILED DESCRIPTION OF THE INVENTION

Definitions

Figure 1:
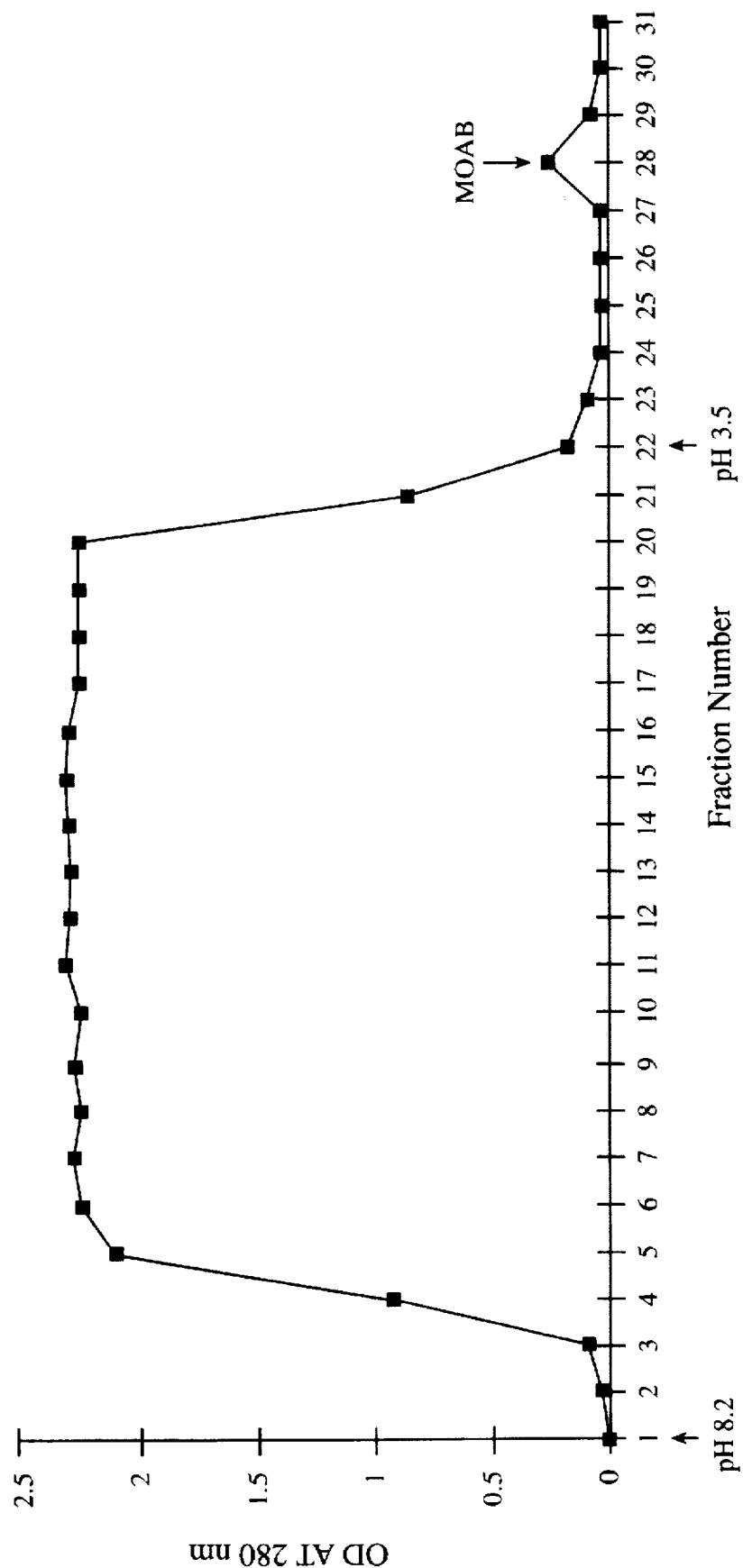
FIG. 1 is a graph illustrating the purification of the monoclonal antibody TB2A36C3 on a protein A-sepharose 4B column.

The following convention is followed to assist in providing a clear and consistent understanding of the scope and detail of the terms:

Amino Acids: Amino acids are shown either by three letter or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Trytophan |
| Y | Tyr | Tyrosine |

B cells: B cells or B lymphocytes secrete proteins/antibodies that protect the human body against infections.

CHARACTERISTICS OF TB2A36C3 ANTIBODY

The monoclonal antibody TB2A36C3, IgA1.k3, shows positive reactivity against both NSCLC and SCLC as seen by ELISA, as well as FACS analysis. Screening for cross reactivity indicated no reactivity against breast, ovary, melanoma, leiomyosarcoma, and leukemia/lymphoma cell lines. The antibody also failed to recognize normal MRC-5 cells as seen by FACS analysis.

Western blot analysis on isolated antigens indicated that the antibody recognized a 32 kD molecular weight antigen on NCIH69 cell line and a cluster of antigens from 28 kD to 106 kD in the NSCLC cell line, NCIH661.

Immunohistochemistry clearly shows that the lung cancer antibody recognized NCIH661 cells, as well as paraffin embedded tissue sections of patients with adenocarcinoma, bronchogenic and squamous cell carcinomas of the lung.

The flow cytometric analysis on living and fixed NCIH661 and NCIH69 shows decrease of antigen positive cells in NCIH661 as a function of in-vitro culturing time. The vice versa was true in case of the SCLC cell line NCIH69. This was observed by both surface and cytoplasmic staining with TB2A36C3.

Cell cycle study DNA histogram showed a gradual increase of cells in G0/G1 and a decrease of cells in S and G2/M in NCIH661 as the cultures aged. The reverse was true in case of SCLC cell line, NCIH69.

TB2A36C3 is capable of proliferating T helper as well as T suppressor cells.

TB2A36C3 exhibits both ADCC, as well as CDC effector functions as seen by chromium release assay and propidium iodide uptake.

DEVELOPMENT OF TB2A36C3, IgA1.k

CELL LINES

The B95-8 cell line maintained in RPMI 1640 and supplemented with 10% FCS was used as a source of Epstein-Barr Virus (EBV).

The human NSCLC (NCIH661) and SCLC (NCIH69) cell lines were obtained from American Type Culture Collection (ATCC) and maintained in culture using RPMI 1640 and 10% FCS.

Lung carcinoma cell lines A-427 was maintained in culture using Eagle's MEM supplemented with non-essential amino acids, sodium pyruvate, basal salt solutions, and 10% FCS.

Autologous lung tumor cell line, SMLU1, was maintained in MEM with 20% FCS. All other ATCC cell lines used in this study were maintained as described.

Unless noted otherwise, the methods used herein are generally well-known to the art. Reference is made to U.S. Pat. Nos. 5,338,661 and 5,348,880, which are incorporated herein by reference only for descriptions of various experimental procedures involving the development, isotyping and quantitation of monoclonal antibodies.

LYMPHOCYTE ISOLATION FROM LYMPH NODES PROXIMAL TO THE TUMOR IN PATIENT WITH NSCLC

Tumor draining lymph nodes obtained from non-small cell lung cancer patient (TB) were cut into fine pieces and meshed through a wire gauze using rubber policeman. Pure B cells were isolated using CD19 coated immunomagnetic beads and were immortalized by EBV. The TB94 human B-cell line was generated by EBV transformation of these CD19+ B-cells according to Henderson et al., 1977 and Katsuki et al., 1977. Here, EBV was used as the transforming agent. It should be apparent that any effective lymphotropic virus or other transforming agent able to transform the B-cells to grow in continuous culture and still produce monoclonal antibodies specific for tumor associated antigens can be used. The EBV transforming process was carried out by resuspending pellets of $5 \times 10^6$ pure B-cells in 1 ml of B95-8 culture supernatant and incubating at 37° C. overnight.

POLYCLONAL RESPONSE

EBV-transformed B cells were washed and plated on a MRC-5 feeder layer coated 96 well culture plate at a cell density of 10,000 to 50,000 cells per well. After one to two weeks, proliferating EBV-transformed B cells were assayed for polyclonal response. They were checked by ELISA on goat anti-human Ig polyvalent and A-427 plates. One method of doing this is as follows: Polycarbonate-coated metallic beads (Bio-EnzaBead™, Litton Bionetics) were incubated with goat antibodies to human immunoglobulins (IgG+IgA+IgM) overnight at 4° C. and then blocked (30 min at room temperature) with 2.5% bovine serum albumin (BSA) to prevent non-specific binding. The beads were then air dried and stored at 4° C. The ELISA for detection of immunoglobulin can be performed as follows. Supernatant fluid from a 96-well culture plate is diluted, incubated with the antibody-capture bead for 1 hr at 37° C., washed, and then incubated for 1 hr at 37° C. with peroxidase-labeled affinity-purified goat antibody to human immunoglobulins (IgG+IgA+IgM). The washed beads are then incubated (10 min at room temperature) with 2,2'-Azino-di[3-ethyl-benzthiazoline-6-sulfonic acid], and the optical density is determined at 405 nm. The immunoglobulin concentrations are interpolated mathematically from the linear portion of a standard curve (30–1000 ng/ml) of human gamma globulin. Supernatant fluids containing>1 mu g/ml are then isotyped using this ELISA with peroxidase-labeled goat antibodies to human gamma, alpha, and mu chains. Subsequent quantitative assays use an immunoglobulin standard appropriate for the monoclonal antibody isotype.

Out of 150 clones assayed, 11 showed high reactivity by ELISA on GAHIg polyvalent and A-427 plates.

DEVELOPMENT OF MONOCLONAL ANTIBODY

Of the eleven, five clones (1A5, 1B3, 1F3, 1F7 and 2A3) showed positive reactivity with autologous tumor cells from TB (SMLU1) as well as small cell lung cancer (SCLC) cell line NCIH69 and were further subjected to limiting dilution for the preparation of the monoclonal antibody.

Limiting dilution of the 2A3 clone was performed on MRC-5 feeder layer. Sixteen clones were picked which showed positive ELISA reaction against goat anti-human GAHIg's polyvalent, NCIH661 and A427 plates. The monoclonal antibody showing maximum reactivity was TB2A36C3.

ISOTYPING AND QUANTITATION OF HUMAN MONOCLONAL ANTIBODY TB2A36C3

The identity of the heavy and light chain compounds of TB2A36C3 was determined by using Ouchterlony immunodiffusion kit (The Binding Site, San Diego, Calif.), following the manufacturer's instructions. An IgA capture ELISA was used to quantitate TB2A36C3 level in supernatant. GAH IgA was used as the capture reagent along with an Alk Phos-labelled GAHIgA conjugate (Caltag Laboratories). Color was developed using para-nitro phenyl phosphate (Sigma Laboratories) in diethanolamine buffer, pH 9.5 and read at 405 mm. The isotype of TB2A36C3 was determined to be IgA1.k.

PURIFICATION OF TB2A36C3

The purification procedures for monoclonal antibodies are well-known. Reference is made to Underwood et al., 1983;

Stephenson et al. 1984; and Ey et al. 1978, which are incorporated herein by reference. TB2A36C3 was purified from culture supernatant using Protein A-Sepharose 4B column pre-equilibrated with 0.1M Borate buffer, pH 8.2. Three grams of the gel matrix was swollen in 0.1M borate buffer. The culture supernatant was passed through the column.

The monoclonal antibody was eluted as a pure fraction from the column using 0.1M Citrate buffer pH 6.5, dialyzed overnight against 0.1M PBS, pH 7.4 buffer. The fraction was concentrated on an Amicon® stir cell concentrator using nitrogen gas and a 43 mm YM10 membrane. Reference is made to FIG. 1.

26.6 micrograms (ug) of the purified TB2A36C3 when used against NCIH661, NCIH69 as well as SMLU1 showed a shift in peak of 72%, 85% and 19% respectively.

Figure 2A:
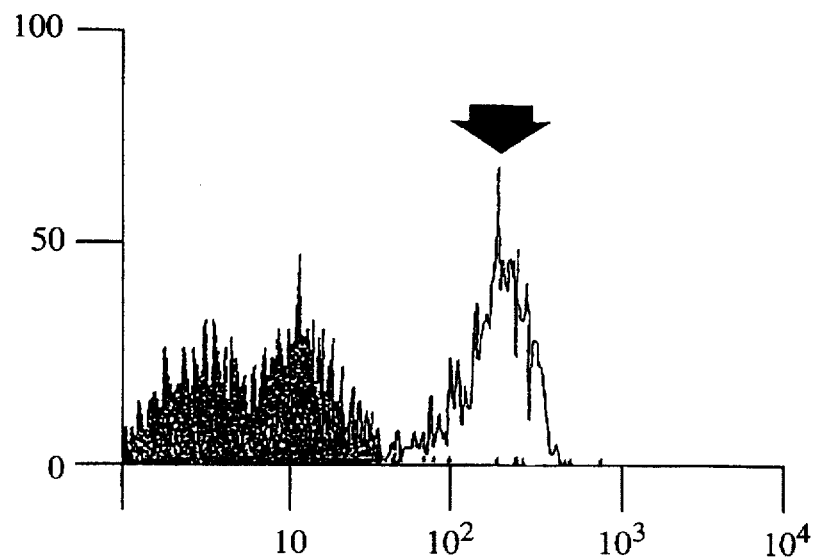
FIG. 2a is a graph which represents the activity of the purified monoclonal antibody TB2A36C3 against small cell lung cancer cell line NCIH69.
Figure 2B:
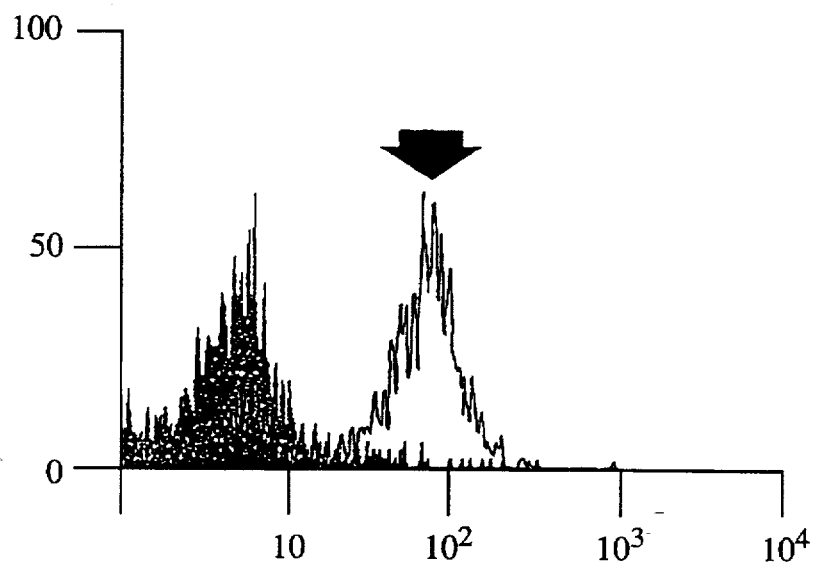
FIG. 2b is a graph which represents the activity of the purified monoclonal antibody TB2A36C3 against non-small cell lung cancer cell line NCIH661.
Figure 2C:
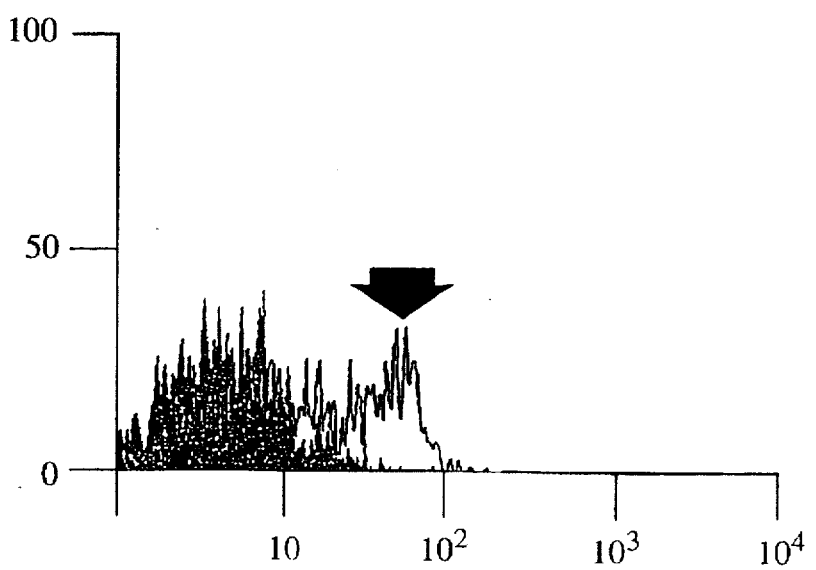
FIG. 2c is a graph which represents the activity of the purified monoclonal antibody TB2A36C3 against autologous tumor cell line SMLU1.

Reference is made to FIGS. 2a, 2b and 2c which represent the activity of the purified monoclonal antibody TB2A36C3 (26.6 ug) against small cell lung cancer cell line NCIH69; non-small cell lung cancer cell line NCIH661; and autologous tumor cell line SMLU1 from the patient.

IMMUNOBLOT AND WESTERN BLOT ANALYSIS

The antigens were isolated from NCIH69, NCIH661 and A427 cells by treatment with buffer containing aprotinin, sodium deoxycholate, Nonidet P-40 (NP40), sodium dodecyl sulfate, leupeptin, iodoacetamide and ethylene diamine tetracetic acid (EDTA).

The isolated antigens were dot blotted on nitrocellulose paper and blocked with PBS-BSA. This was incubated for 4 hours at room temperature with 25 ug of purified monoclonal antibody TB2A36C3, washed 10 times with PBS and then incubated with Alkaline Phosphatase (Alk-Phos) conjugated goat anti-IgA antibody for 2 hours. Finally, the reaction was developed by a substrate containing Nitroblue Tetrazolium (NBT) and 5-bromo-4-chloro-3-indolyl phosphate (BCIP). The cells were grown on slides and fixed with ethanol.

Figure 3A:
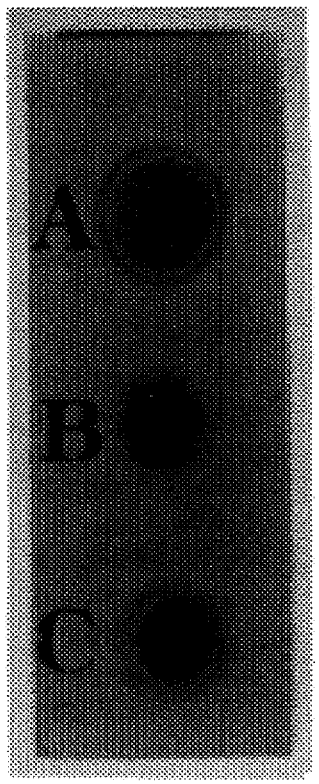
FIG. 3a is a photograph of a dot blot of extracted antigen from NCIH69 (A), NCIH661 (B) and A427 (C) cell lines.
Figure 3B:
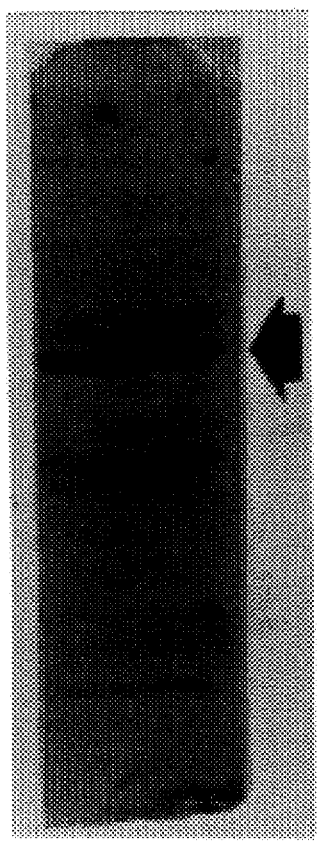
FIG. 3b is a photograph of a Western blot of the extracted antigen from NCIH69 cell line.
Figure 3C:
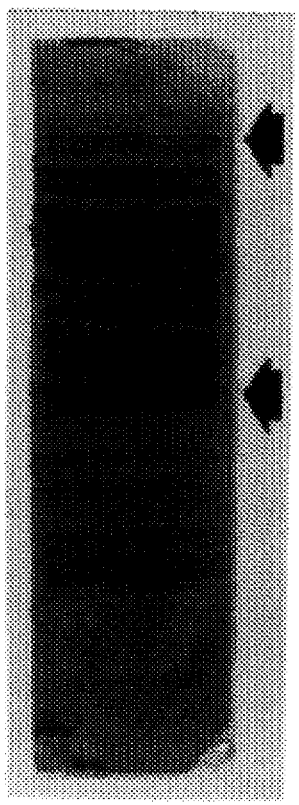
FIG. 3c is a photograph of a Western blot of the extracted antigen from NCIH661 cell line.

Reference is made to FIG. 3a, which illustrates dot blotting of extracted antigen from NCIH69 (A), NCIH661 B) and A427 (C) cell lines. Reaction with lung cancer antibody TB2A36C3 shows high recognition of the antigens NCIH69 (A) and NCIH661 (B), and weakly reactive with A427 (C). FIGS. 3b and 3c are Western blots of the extracted antigens where a 32 kD antigen is recognized by TB2A36C3 in SCLC cell line NCIH69. The arrow in FIG. 3b indicates a 32 kD antigen TB2A36C3 recognizes in the NCIH69 line. The arrows in FIG. 3c indicate a cluster of antigens from 28–106 kD which TB2A36C3 recognizes in the NCIH661 cell line.

Cross-reactivity of TB2A36C3 was screened against a panel of human cell lines. Table 1 demonstrates the screening of TB2A36C3 clone against different cell lines.

TABLE 1

| CELL LINES | CONT. | AFTER 2 HRS | SIGN |
| --- | --- | --- | --- |
| LS174T | 0.034 | 0.053 | − |
| HT 29 | 0.040 | 0.162 | +++ |
| CACO 2 | 0.842 | 1.119 | + |
| COLO 205 | .02 | 4.0 | +++ |
| NCIH661 | 0.054 | 0.093 | ++ |
| SKBR-3 | 0.140 | 0.161 | − |
| A498 | 0.020 | 0.056 | − |

TABLE 1-continued

| CELL LINES | CONT. | AFTER 2 HRS | SIGN |
| --- | --- | --- | --- |
| SKLMS-1 | 0.048 | 0.072 | − |
| SKLMEL-31 | 0.020 | 0.044 | − |
| MCF-7 | 0.034 | 0.052 | − |
| SKOV-3 | 0.096 | 0.122 | − |
| NCIH69 | 0.2 | 3.2 | +++ |
| MOLT-4 | 0.3 | 0.2 | − |
| CALU-1 | 0.071 | 0.085 | − |
| RAJI | 0.4 | 0.6 | − |

TB2A36C3 was reactive with 5 of 14 cell lines tested, including colon (HT29, COLO205, CACO2), lung (NCIH661, NCIH69), and kidney (A498).

TB2A36C3 was not reactive with breast, ovary, melanoma, leiomyosarcoma and leukemia/lymphoma cell lines, with normal MRC-5 (FACS analysis), and with cells from some of the excretory organs namely kidney and liver (immunohistochemistry).

IMMUNOPEROXIDASE STAINING OF TUMOR CELLS AS WELL AS TUMOR SECTIONS

NCIH661 and MENMEL cells were grown on slides and fixed with cold acetone. Cells were rehydrated with decreasing grades of ethanol, blocked with goat and human sera and were incubated with the TB2A36C3 antibody for 2 hours and then with biotinylated second antibody for ½ hour. Finally, they were treated with avidin-biotin complex for 30 minutes and stained with diamino benzidine (DAB), which is used as substrate. Intense brown staining is witnessed if the antibody reacts positively as seen on NCIH661 wells but not on MENMEL (negative control).

Paraffin embedded sections from lung tumor tissue, as well as normal subjects were obtained. These sections were deparaffinized with xylene and rehydrated with grades of ethanol. They were then incubated with TB2A36C3 for 2 hours, washed and then incubated with biotinylated second antibody for ½ hour. Finally, they were treated with avidin biotin complex for 30 minutes. Positive reactivity is seen under the microscope when stained with a substrate containing DAB. Negative staining is seen in control normal lung sections. All sections, as well as cells, were counterstained by Richard Allan's hematoxylin.

REACTIVITY OF FIXED VS. LIVING CELLS

TB2A36C3 was tested by indirect immunofluorescence cytometry (Chang et al., 1994) on living and fixed NCIH69 and NCIH661 cells. The representative bindings of the antibody to the viable and fixed cells is illustrated in Table 2 as follows:

TABLE 2

ACTIVITY OF TB2A36C3 AGAINST LUNG CARCINOMA CELL LINES

| CELL LINE | 1 DAY CULTURE | | 3 DAY CULTURE | | 5 DAY CULTURE | |
| --- | --- | --- | --- | --- | --- | --- |
| | CYT. | SURFACE | CYT. | SURFACE | CYT. | SURFACE |
| NCIH69 | 97.7% | 23% | 81% | 19% | 69% | 31% |
| NCIH661 | 5% | 95% | 61% | 39% | 85% | 15% |

A decrease of antigen positive cells as a function of in-vitro culturing time was observed by both surface and cytoplasmic staining of NCIH661 cells. However, the opposite was true for NCIH69 cells. The flow cytometric analysis of 1, 3 and 5 day old cultures of NCIH661 and NCIH69 and SCLC antigen in relationship to DNA content is illustrated in Table 3 as follows:

TABLE 3

DNA CELL CYCLE ANALYSIS OF LUNG CARCINOMA CELL LINES

| TUMOR CELLS | DAYS OF CULTURE | % G0/G1 | % S | % G2/M |
|---|---|---|---|---|
| NCIH69 | 1 | 49 | 30 | 21 |
|  | 3 | 55.7 | 29.2 | 15.1 |
|  | 5 | 42.2 | 43.4 | 14.4 |
| NCIH661 | 1 | 18.1 | 76.4 | 5.6 |
|  | 3 | 35.0 | 56.0 | 9.0 |
|  | 5 | 70.6 | 25.6 | 3.8 |

Table 3 shows that both the analyses were detected throughout all phases of the cell cycle. This finding suggests that synthesis of the antigens occurs in the G1 phase and persists thereafter. Cell cycle study of DNA histogram of NCIH661 showed a gradual increase of cells in accumulation of quiescent cells (G0 and deep G1) may correspond with the absence of detectable NSCLC antigen in large numbers of cells of old cultures. However, the vice versa was true in case of the SCLC cell line NCIH69.

Figure 4A:
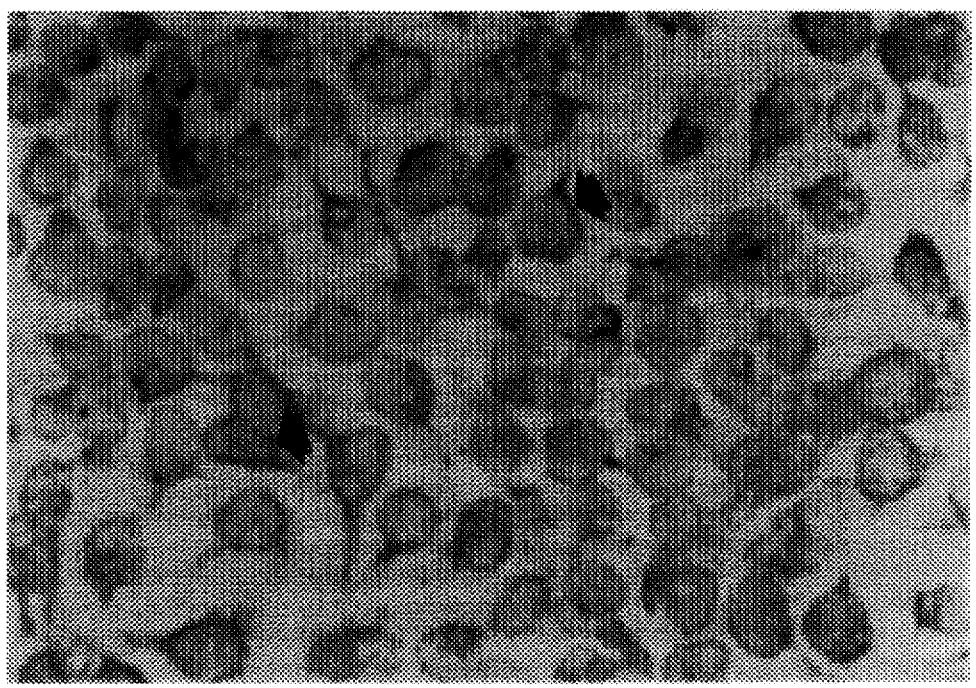
FIGS. 4a and 4b illustrate immunoperoxidase staining of paraffin embedded tissue sections from a patient with lung carcinoma (FIG. 4a), as well as from a normal lung (FIG. 4b). Intense DAB staining of the lung tumor antigen is noted around the ductal region (FIG. 4a). No staining of the normal lung section is noted (FIG. 4b).
Figure 4B:
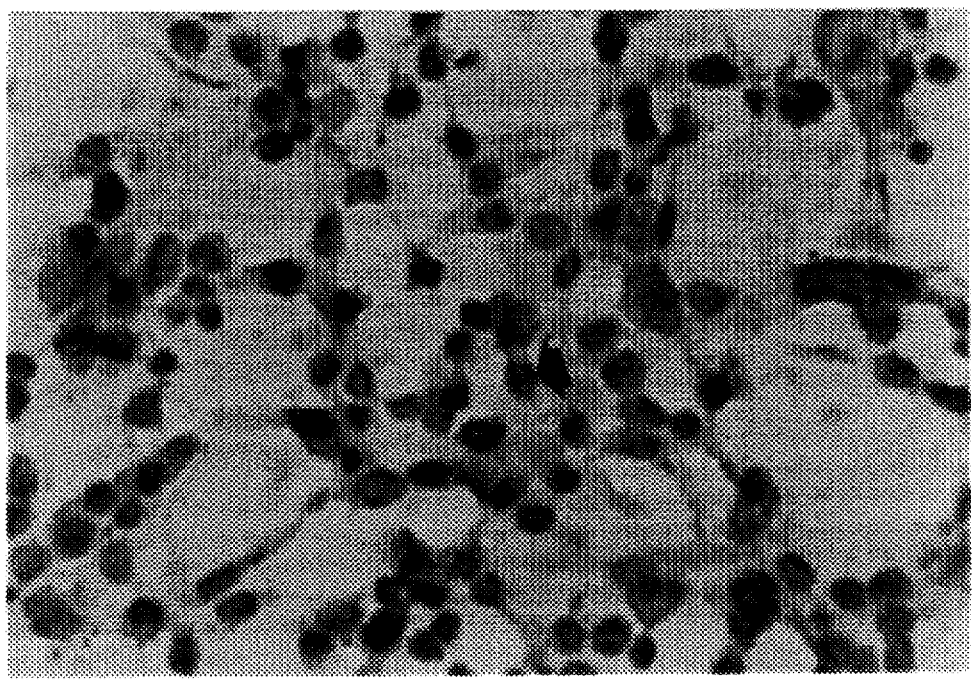
Figure 5A:
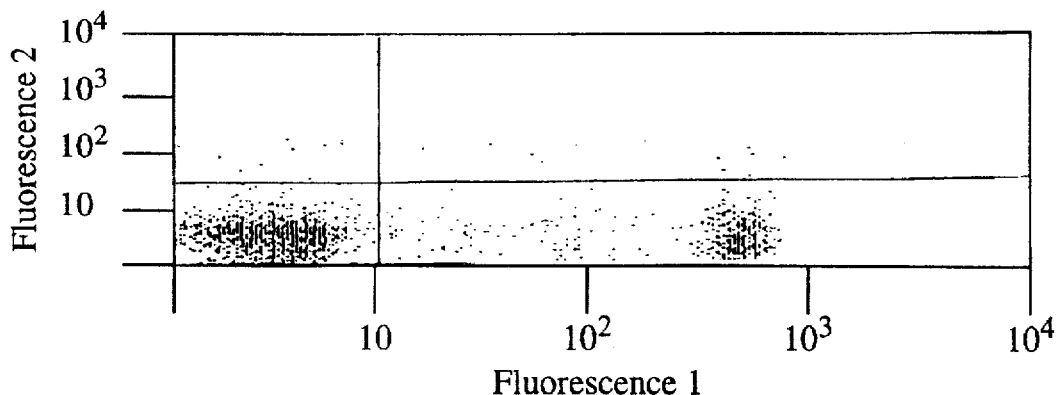
FIG. 5a is a graph depicting a control group for the proliferation of a CD8 cell population.
Figure 5B:
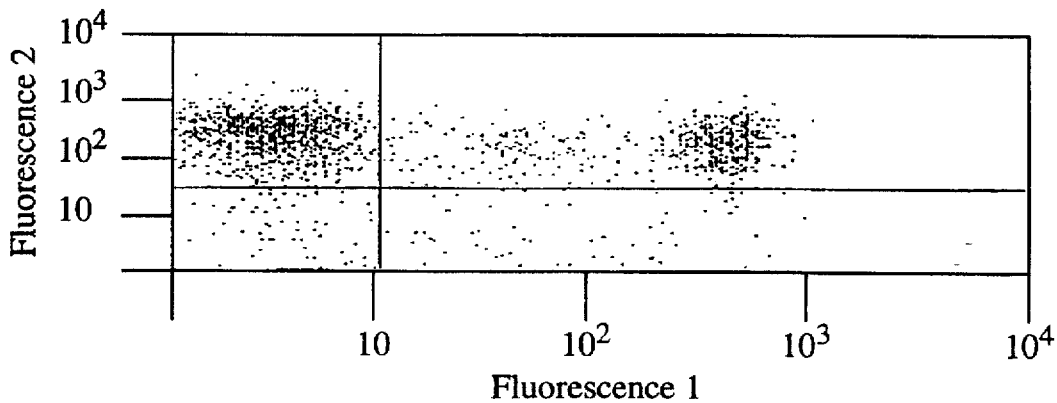
FIG. 5b is a graph depicting a control group for the proliferation of another CD8 cell population.
Figure 5C:
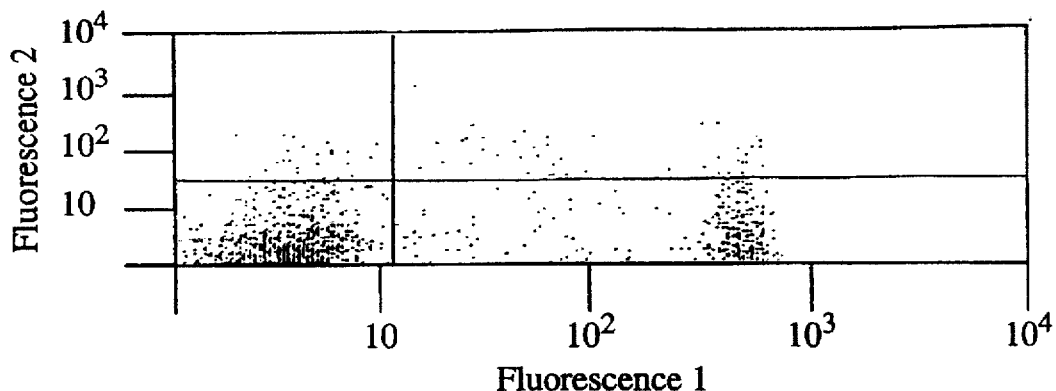
FIG. 5c is a graph depicting the proliferation of a CD8 cell population in the presence of a 25 µg/ml concentration of TB2A36C3.
Figure 5D:
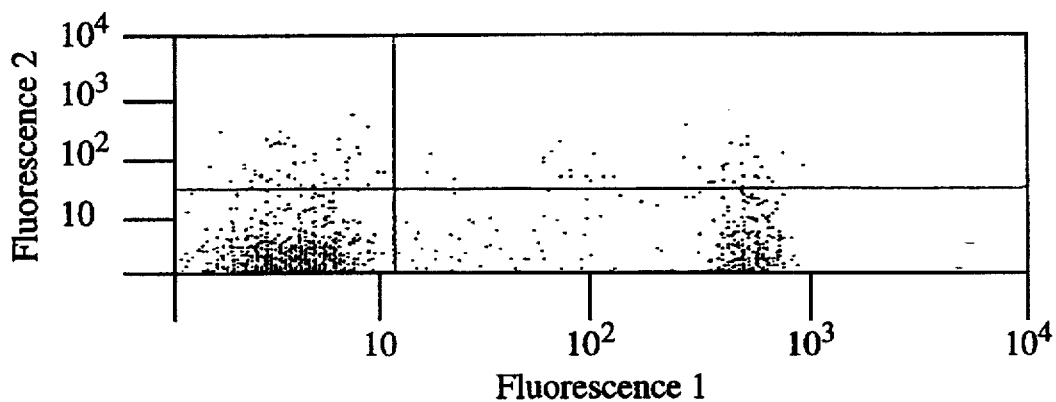
FIG. 5d is a graph depicting the proliferation of a CD8 cell population in the presence of a 50 µg/ml concentration of TB2A36C3.
Figure 6A:
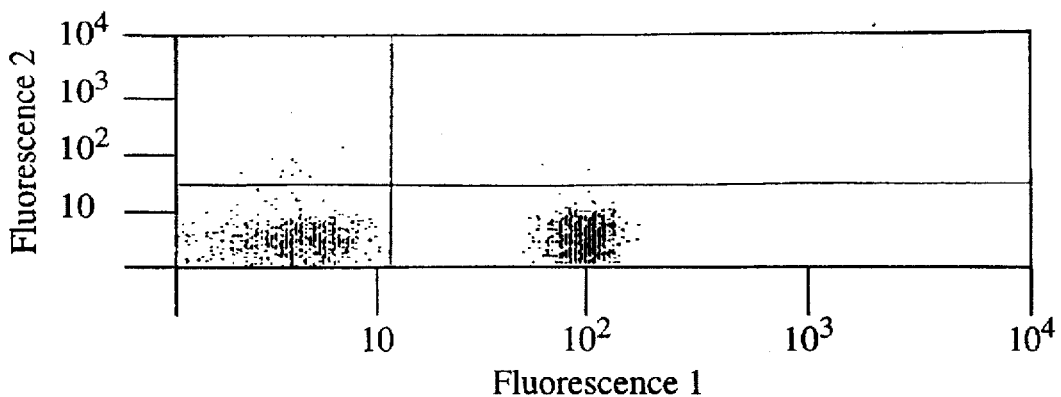
FIG. 6a is a graph depicting a control group for the proliferation of a CD4 cell population.
Figure 6B:
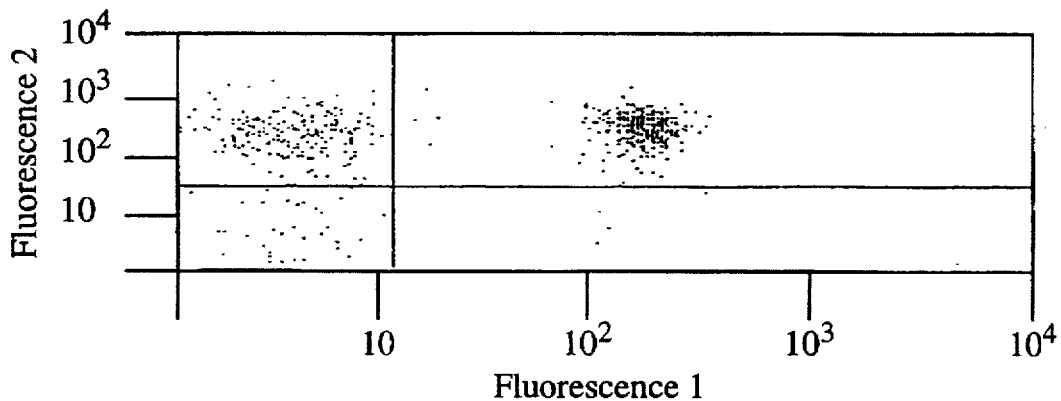
FIG. 6b is a graph depicting a control group for the proliferation of another CD4 cell population.
Figure 6C:
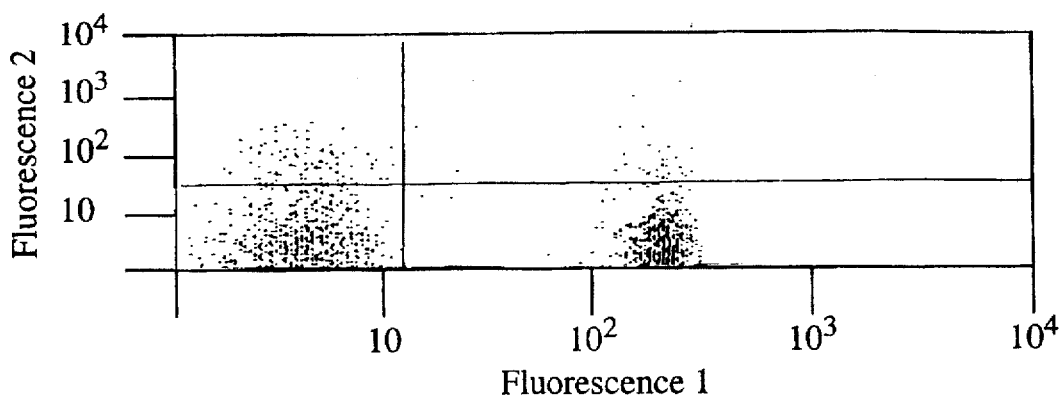
FIG. 6c is a graph depicting the proliferation of a CD4 cell population in the presence of a 50 µg/ml concentration of TB2A36C3.
Figure 6D:
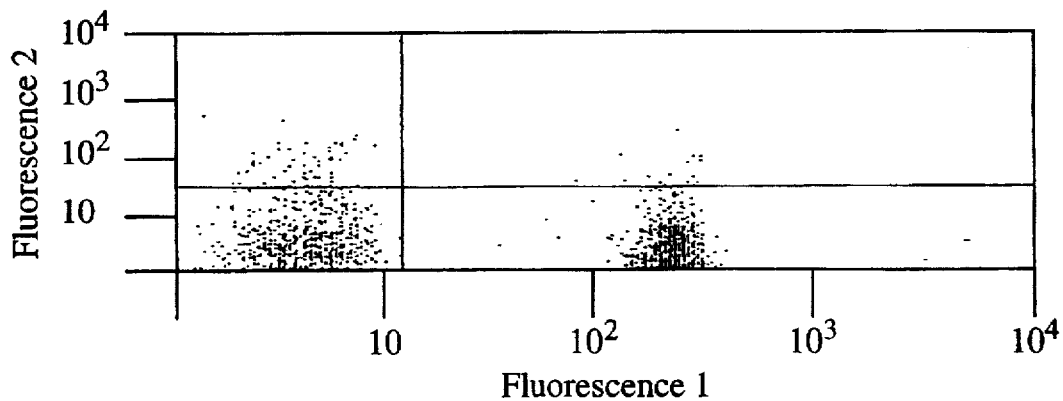
FIG. 6d is a graph depicting the proliferation of a CD4 cell population in the presence of a 25 µg/ml concentration of TB2A36C3.

FIGS. 4a and 4b illustrate immunoperoxidase staining of NCIH661 cells by the lung cancer antibody TB2A36C3. Intense Diamino-benzidine (DAB) staining of the lung tumor antigen on NCIH661 cells is noted as shown by the arrow. Also, no staining of MENMEL is seen because of the absence of the antigen.

CELL PROLIFERATION ASSAY

The capability of TB2A36C3 in proliferating CD4+ and CD8+ lymphocytes in whole blood was determined by flow cytometry using anti-CD69/CD8/CD4 antibody following standard protocol of Becton Dickinson.

FIGS. 5a, 5b, 5c and 5d clearly show the demonstration of the proliferation of CD8 population using TB2A36C3 as seen in the gated cells in the upper right quadrant. As compared to 0.64 of percent gated cells in control, the TB2A36C3 antibody resulted in a proliferation of 2.04 when reacted with 25 ug and 2.40 when reacted with 50 ug of TB2A36C3.

FIGS. 6a, 6b, 6c and 6d clearly show the demonstration of the proliferation of CD4 population using TB2A36C3 as seen in the gated cells in the upper right quadrant. As compared to 0.10 of percent gated cells in control, the TB2A36C3 antibody resulted in a proliferation of 1.15 when reacted with 25 ug and 1.21 when reacted with 50 ug of TB2A36C3.

COMPLEMENT MEDIATED LYSIS

Lysis was determined using $^{51}Cr$ release assay with rabbit complement. NCIH661, SMLU1, and MCF-7 were labelled with $^{51}Cr$ (75 uCi/$10^6$ cells) sodium chromate at 37° C. for two hours. The cells were then washed two times with RPMI 1640. $^{51}Cr$ labelled cells (5×$10^4$) were incubated with 25 ug of TB2A36C3+serial dilutions of rabbit complement for four hours. Thereafter supernatants were harvested and $^{51}Cr$ release measured.

This data was compared to spontaneous release, as well as maximal release after incubation of $^{51}Cr$ cells with 5% Triton X-100. Specific CML was determined as follows:

$$\% \text{ Cell Lysis} = \frac{\text{Experimental }^{51}\text{Cr release} - \text{Spontaneous }^{51}\text{Cr release}}{\text{Maximal }^{51}\text{Cr release} - \text{Spontaneous }^{51}\text{Cr release}} \times 100$$

Effector functions of the antibody were checked by complement dependent cytotoxicity against SMLU1 and SKBR3 as illustrated in the following Table 4:

TABLE 4

RADIOACTIVE COUNTS OF CHROMIUM 51 RELEASED AFTER COMPLEMENT MEDIATED LOSS

| | EXPERIMENTAL | | | | CONTROL | | |
|---|---|---|---|---|---|---|---|
| COMP | TB2A36C3 (50UG) | | TB2A36C3 (25UG) | | ISOTYPE MATCHED | SPONT RELEASE | SPONT RELEASE |
| DILN | SMLU1 | SKBR-3 | SMLU1 | SKBR-3 | IgA Ig | RPMI | PBS-BSA |
| 1:2 | 18,813 | 6,489 | 17,338 | 5,071 | 16,062 | 14,060 | 13,436 |
| 1:4 | 18,881 | 5,140 | 16,717 | 5,105 | 16,048 | | |
| 1:8 | 16,155 | 4,790 | 16,290 | 6,314 | 16,025 | | |

Preliminary data show a decrease in percent lysis from 20 TO 3.5 with a concomitant decrease in the complement concentration thereby indicating CDC activity of TB2A36C3 as illustrated in the following Table 5:

TABLE 5

PERCENT COMPLEMENT MEDIATED LYSIS BY TB2A36C3 ANTIBODY

| COMPLETE DILUTION | TB2A36C3 (50UG) | | TB2A36C3 (25UG) | | ISOTYPE MATCHED |
|---|---|---|---|---|---|
| | SMLU1 | SKBR-3 | SMLU1 | SKBR-3 | IgA Ig |
| 1:2 | 20% | 0% | 21.6% | 0% | 8.5% |
| 1:4 | 8.1% | 0% | 5.5% | 0% | 3.4% |
| 1:8 | 8.2% | 0% | 4.5% | 0% | 5.6% |
| 1:16 | 3.5% | 0% | 3.8% | 0% | 3.3% |

ANTIBODY DEPENDENT CELL MEDIATED CYTOTOXICITY

Cytotoxic T cells were harvested from whole blood using CD8+ immunomagnetic beads. 4×$10^5$ T cells stimulated with 25 ug antibody was added to the target cells (NCIH661, SMLU1, and MCF-7) at a effector/target ratio of 40:1 and 20:1 and incubated at 37° C. for 4 hours. Dead target cells were then measured by flow cytometric analysis using propidium iodide uptake as illustrated in FIGS. 7a, 7b, 7c, 8a, 9b, 9a, 9b and 9c.

Figure 7A:
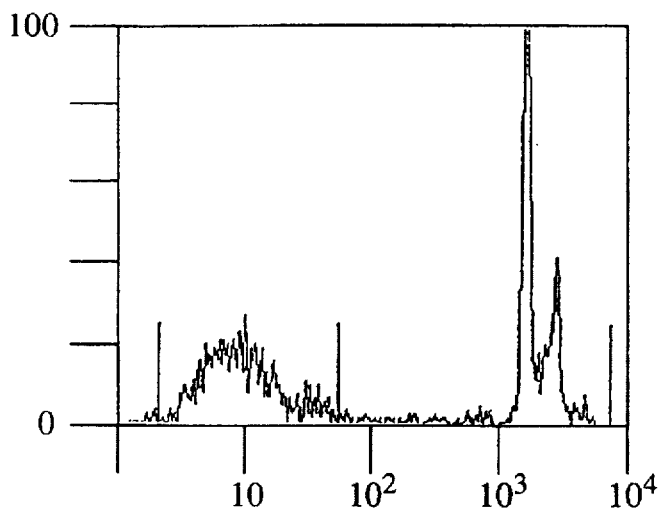
FIG. 7a is a control histogram for antibody-dependent cell- mediated cytotoxicity (ADCC) using MCF7 and CD8 cells in phosphate buffered saline
Figure 7B:
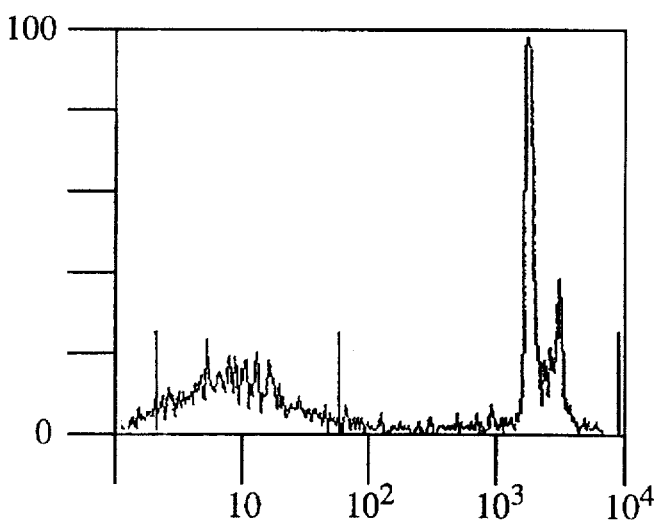
FIG. 7b is a histogram depicting an antibody-dependent cell mediated cytotoxicity test using cytotoxic T-cells stimulated with 25 µg/ml TB2A36C3 and exposing the T-cells to MCF7 and CD8 cells at a ratio of 20 to 1.
Figure 7C:
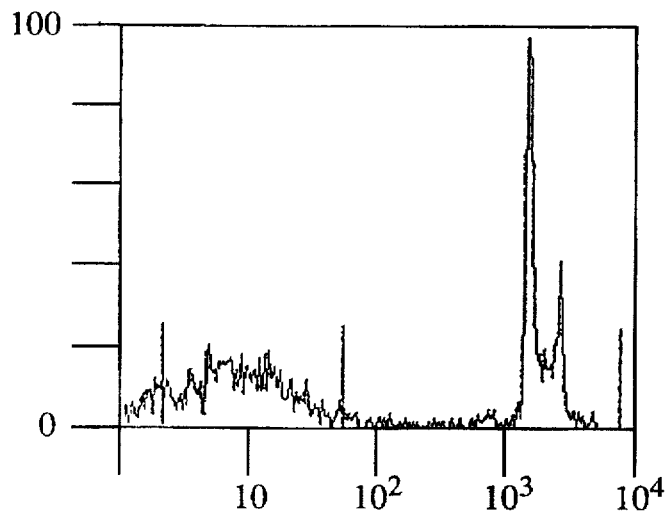
FIG. 7c is a histogram depicting an antibody-dependent cell mediated cytotoxicity test using cytotoxic T-cells stimulated with 25 µg/ml TB2A36C3 and exposing the T-cells to MCF7 and CD8 cells at a ratio of 40 to 1.

FIGS. 7a, 7b and 7c are histograms from control MCF-7 cells showing no antigen dependent cell mediated cytoxicity (ADCC). As indicated in the bottom right square (% total), there is no change in the propidium iodide uptake when effector/target ratio is 20:1 (FIG. 7b) and 40:1 (FIG. 7c) was compared to control FIG. 8a).

Figure 8A:
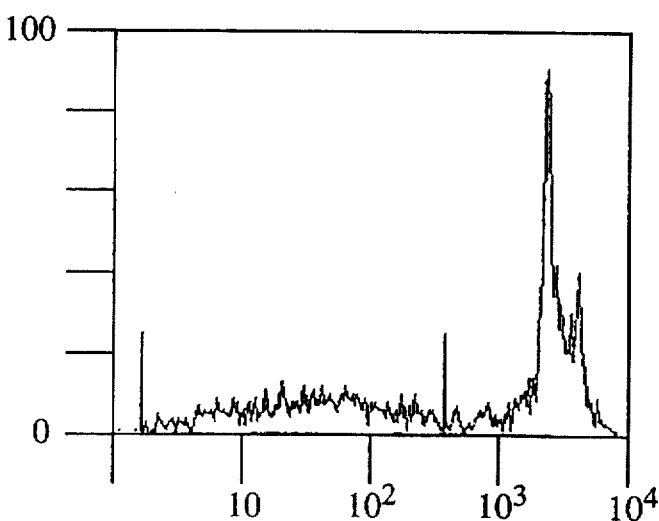
FIG. 8a is a histogram depicting an antibody-dependent cell mediated cytotoxicity test using cytotoxic T-cells stimulated with 25 µg/ml TB2A36C3 and exposing the T-cells to CD8 and NCIH661 cells at a ratio of 40 to 1.
Figure 8B:
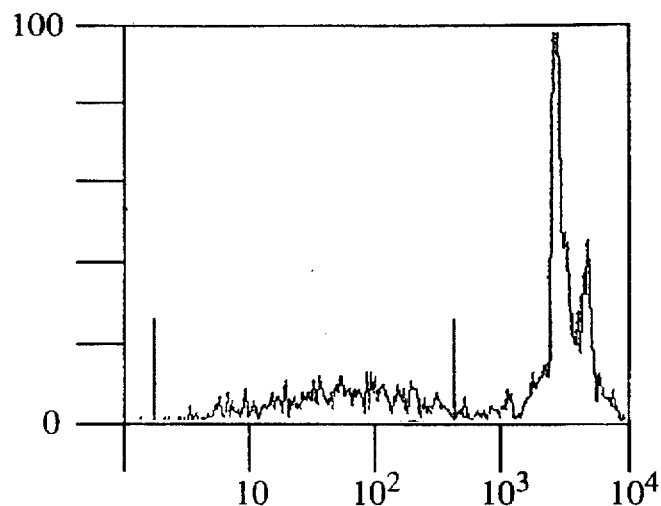
FIG. 8b is a histogram depicting an antibody-dependent cell mediated cytotoxicity test using cytotoxic T-cells stimulated with 25 µg/ml TB2A36C3 and exposing the T-cells to CD8 and NCIH661 cells at a ratio of 20 to 1.

FIGS. 8a and 8b are histograms which show positive ADCC activity of TB2A36C3 activated CD8+ cells with NCI661 cells.

Figure 9A:
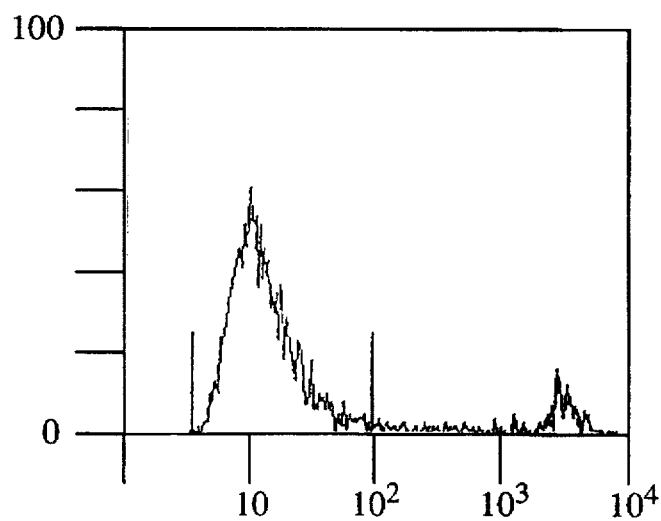
FIG. 9a is a control histogram of cell growth for autologous tumor cells SMLU1 and CD8 cells in phosphate buffered saline.
Figure 9B:
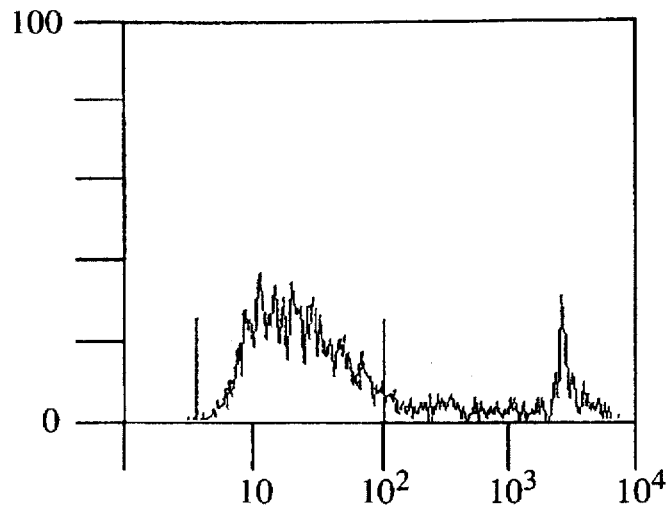
FIG. 9b is a histogram depicting an antibody-dependent cell mediated cytotoxicity test using cytotoxic T-cells stimulated with 25 µg/ml TB2A36C3 and exposing the T-cells to CD8 and SMLU1 cells at a ratio of 20 to 1.
Figure 9C:
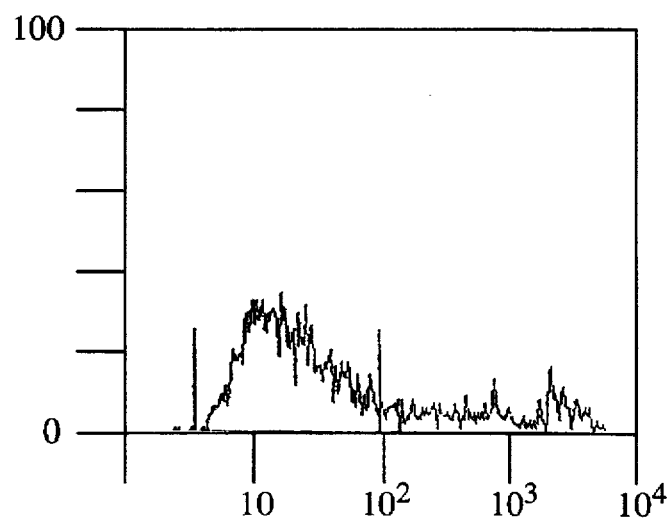
FIG. 9c is a histogram depicting an antibody-dependent cell mediated cytotoxicity test using cytotoxic T-cells stimulated with 25 µg/ml TB2A36C3 and exposing the T-cells to CD8 and SMLU1 cells at a ratio of 40 to 1.

FIGS. 9a, 9b and 9c are histograms from autologous tumor cells (SMLU1) showing positive ADCC activity. Increase in propidium iodide uptake is seen (FIGS. 9b and 9c) when TB2A36C3 activated CD8+ cells were incubated with SMLU1 cells as compared to control (FIG. 9a).

SEQUENCING THE LIGHT CHAIN OF THE ANTIBODY TB2A36C3

The total RNA was isolated from $2 \times 10^8$ EBV-transformed cells secreting the antibody TB2A36C3. From this, mRNA was isolated and cDNA prepared using reverse transcriptase enzyme. This cDNA was amplified by polymerase chain reaction (PCR) under the conditions 94° C.—1 min, 55° C.—1 min., 72° C.—2 min. for 30 cycles. The 5' primer sequence was: 5'—GGG AAT TCA TGG ACA TG(AG) (AG)(AG)(AGT)(CT) CC (ACT) (ACG) G (CT)(GT) CA (CG) CTT—3' [SEQ. ID. NO. 1]. The 3' primer sequence was 5'-CCA AGC TTC ATC AGA TGG CGG GAA GAT'-3' [SEQ. ID. NO. 2].

After amplification, the light chain was electrophoresed on a 1.5% agarose gel containing ethidium bromide and amplified light chain visualized under a UV transilluminator. This DNA was then ligated onto a plasmid DNA. The construct was transformed into an *E. coli* (HB101 competent cells) and sequenced by Sangers dideoxy method (Sanger, F. et al., 1977) using $S^{35}$. The nucleotide sequence of the light chain of the TB2A36C3 antibody is shown in FIG. 10 [SEQ. ID. NO. 3]. The amino acid sequence is shown in SEQ. ID. NO. 4.

BIOREAGENTS

The peptide fragment F(ab)'$_2$ of TB2A36C3 can be isolated by high pressure liquid chromatography (HPLC) after papain digestion of the whole antibody and used for detection of lung carcinoma circulating antigens. The monoclonal antibodies can be used in test kits which are used to diagnose clinically suspected cases of lung carcinoma.

Any of a large number of clinical tests may be employed utilizing the monoclonal antibody TB2A36C3 of this invention. Typical tests include radioimmunoassay, enzyme-linked-immunoassay (ELISA), precipitation, agglutination, direct and indirect immunofluorescence and complement fixation. These tests may employ competitive and sandwich-type assays.

TB2A36C3 is tested for specificity by ELISAs and by immunoblotting of a variety of enterics. By these means, it can be determined that the antibody forms a strong reaction by direct ELISA with tumor-associated antigens.

ELISAs are a conventional method for assaying for the presence of an antigen in a sample of test material. The sandwich ELISA of the invention is adapted to assay for the presence of tumor-associated antigens in a sample of test material and includes the following steps: First, a known antibody to tumor-associated antigens is bound to a suitable adsorbtor substrate. Preferably, a plastic culture plate is used, such as a 96-well polystyrene culture plate (Costar, Cambridge, Mass.—Model No. 3596). A solution of antibody to tumor-associated antigens is placed in each of the wells and allowed to remain under conditions such that the antibody to tumor-associated antigens is adsorbed to the surface of the wells. Unadsorbed antibody solution is then washed away, leaving the antibody to tumor-associated antigens bound to the adsorptive walls of the wells, which shall be referred to as "adsorbtor substrate units." With antibody to tumor-associated antigens adsorbed to them, they shall be referred to as "antibody to tumor-associated antigen substrate units." The antibody to tumor-associated antigen substrate units is then treated with an appropriate blocking reagent, such as nonfat dried milk, to block non-specific binding sites. After appropriate incubation, this reagent is removed.

Next, a known quantity of the test material is exposed to the antibody to tumor-associated antigen-charged substrate units for an appropriate period of time, and then is removed by washing. Any tumor-associated antigens in the test material will bind to the antibody to charged substrate units.

Similarly, a standard preparation of tumor-associated antigens is exposed to another set of antibodies to tumor-associated antigen-charged substrate units to serve as a control.

A second alkaline-phosphatase conjugated antibody is added to tumor-associated antigen-charged substrate units to bind with any bound tumor-associated antigens. After appropriate incubation, the unbound second antibody is removed by washing.

The antibody to tumor-associated antigen-charged substrate units are reacted with test samples of tumor-associated antigens and are then assayed for the presence of the antibody.

Preferably this is done by exposing antibody to tumor-associated antigen-charged substrate units reacted with the test samples or tumor-associated antigens and the antibody thereon to a marker-coupled anti-human antibody to allow the marker-coupled antibody to bind to any antibody present. The unbound marker-coupled antibody is then removed, and the amount of marker remaining on the antibody to tumor-associated antigen-charged substrate units is measured. The marker may be an enzyme measured by its effect on a selected reagent, a fluorescent material, a radioactive material, or any other of the markers familiar to one skilled in the art. It will be apparent that the antibody itself may be combined directly with a marker, whereupon the step of reacting a marker-coupled anti-human antibody may be omitted.

The antibody may also be used in other conventional ELISAs. For example, a sample of test material may be bound to an adsorbtor substrate and then exposed to the antibody disclosed above. The antibody binds to any tumor-associated antigens present in the test material. Unbound portions of the antibody are then removed. Next, an assay comparable to those discussed above is conducted for the presence of bound antibody.

The present invention also includes kits, e.g., diagnostic assay kits, for utilizing the antibody to tumor-associated antigens and carrying out the method disclosed above. In one embodiment, the diagnostic kit would conventionally include the monoclonal antibody TB2A36C3 in one or more containers, a conjugate of a specific binding partner for the antibody, a label capable of producing a detectable signal, and instructions for its use. The kit may be conjugated to a label, as is well known to the art. Various labels include enzymes, radioisotopes, particulate labels, chromogens, fluorescers, chemiluminescers, coenzymes, free radicals, and bacteriophages. Additionally the antibody may be bound to a support.

The instructions for use are suitable to enable an end user to carry out the desired test. By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like. It is within the scope of this invention to provide manual test kits or test kits for use in automated analyzers.

It is understood that the present invention is not limited to the particular reagents, steps or methods disclosed herein. Instead it embraces all such modified forms thereof as come within the scope of the claims following the Bibliography.

BIBLIOGRAPHY

Chang, H. R. et al., 1994, "Tumor Associated Antigens Recognized by Human Monoclonal Antibodies," *Ann. Surg. Oncol.*, 1(3):213–221.

Ey, P. L. et al., 1978, "Isolation of Pure $IgG_{1a}$, $IgG_{2a}$ and $IgG_{2b}$ Immunoglobulins from Mouse Using Protein A-Sepharose," *Immunochemistry*, 15:429–436.

Henderson, E. et al., 1977, "Efficiency of Transformation of Lymphocytes by EBV," *Virology*, 76:152–163.

Katsuki, T. et al., 1977, "Identification of the Target Cells in Human B Lymphocytes for Transformation by EBV," *Virology*, 83:287–294.

Sanger, F. et al., 1977, "DNA Sequencing With Chain-terminating Inhibitors," *PNAS, USA*, 74:5463–5467.

Stephenson, J. R., et al., 1984, "Production and Purification of Murine Monoclonal Antibodies; Aberrant Elution from Protein A Sepharose CL-4b," *Anal. Biochem.*, 142:189–195.

Underwood, P. A. et al, 1983, "Use of Protein A to Remove Immunoglobulins from Serum in Hybridoma Culture Media," *J. Immunol. Methods*, 60:33–45.

---

What is claimed:

1. A monoclonal antibody designated TB2A36C3 isolated from an Epstein-Barr virus-transformed human B-cell line designated TB94 and deposited with the American Type Culture Collection and bearing Accession Number CRL-12142, wherein the monoclonal antibody is specifically reactive against lung tumor antigens.

2. A transformed human B-cell line immortalized by Epstein-Barr virus, deposited with the American Type Culture Collection and bearing the Accession Number CRL-12142.

3. A human monoclonal antibody isolated from an Epstein-Barr virus-transformed human B-cell line deposited with the American Type Culture Collection and bearing Accession Number CRL-12142 which shows positive reactivity against non-small cell lung cancer and small cell lung cancer and which shows no reactivity against breast, ovary, melanoma, leiomyosarcoma and leukemia/lymphoma cell lines.

4. The monoclonal antibody according to claim 3, wherein the antibody specifically binds to a 32 kD molecular weight antigen on NCIH69 (ATCC HTB-119) cells and a cluster of antigens of from 28 kD to 106 kD on non-small cell lung cancer NCIH661 (ATCC HTB-183) cells as measured by Western blot analysis.

5. A bioreagent for antibody assays comprising a F(ab')₂ fragment of the monoclonal antibody designated TB2A36C3 isolated from an Epstein-Barr virus-transformed human B-cell line deposited with the American Type Culture Collection and bearing Accession Number CRL-12142.

6. The monoclonal antibody according to claim 1, having an amino acid sequence identical to SEQ. ID. NO: 3.

7. A diagnostic aid for non-small cell lung cancer or small cell lung cancer, the diagnostic aid comprising a monoclonal antibody isolated from an Epstein-Barr virus-transformed human B-cell line deposited with the American Type Culture Collection and bearing Accession Number CRL-12142 and a carrier.

8. A method of screening a sample of patient's sera or tissue for the presence of a carcinoma-associated antigen which comprises contacting a sample of serum or tissue with the monoclonal antibody of claim 3 and detecting the binding of the antibody to the antigen present in the sample.

9. The method of claim 8 in which a second antibody which shows positive reactivity against non-small cell lung cancer and small cell lung cancer and which shows no reactivity against breast ovary, melanoma, leiomyosarcoma and leukemia/lymphoma cell lines is also contacted with the sample, the second antibody being coupled to a solid support.

10. The method of claim 8 wherein the carcinoma is a non-small cell lung cancer or a small cell lung cancer.

11. An in vitro method for activating CD4 or CD8 cells comprising exposing the cells to an activating amount of the antibody according to claim 3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: C-terminal ( x i ) SEQUENCE DESCRIPTION: SEQ ID NO:1:

```
GGGAATTCAT GGACATGAGA GAGAGTCTCC ACTACGGCTG TCACGCTT          4 8
```

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: C-terminal ( x i ) SEQUENCE DESCRIPTION: SEQ ID NO:2:

```
CCAAGCTTCA TCAGATGGCG GGAAGAT          2 7
```

( 2 ) INFORMATION FOR SEQ ID NO:3:

( i ) SEQUENCE CHARACTERISTICS:
  ( A ) LENGTH: 402 base pairs
  ( B ) TYPE: nucleic acid
  ( C ) STRANDEDNESS: single
  ( D ) TOPOLOGY: linear ( i i ) MOLECULE TYPE: cDNA ( v ) FRAGMENT TYPE: C-terminal ( i x ) FEATURE:
  ( A ) NAME/KEY: CDS
  ( B ) LOCATION: 1..402

( x i ) SEQUENCE DESCRIPTION: SEQ ID NO:3:

```
ATG GAA ACC CCA GCG CAG CTT CTC TTC CTC CTG CTA CTC TGG CTC CCA      48
Met Glu Thr Pro Ala Gln Leu Leu Phe Leu Leu Leu Leu Trp Leu Pro
 1               5                  10                  15

GAT ACC ACC GGA GAA ATT GTG TTG ACG CAG TCT CCA GGT ACC CTG TCT      96
Asp Thr Thr Gly Glu Ile Val Leu Thr Gln Ser Pro Gly Thr Leu Ser
                20                  25                  30

TTG TCT CCA GGG GAA AGA GCC ACC CTC TCC TGC AGG GCC AGT CAG AGT     144
Leu Ser Pro Gly Glu Arg Ala Thr Leu Ser Cys Arg Ala Ser Gln Ser
            35                  40                  45

TTT AGC AGA AGC TTC TTA GCC TGG TAC CAG CAG AAA CCT GGC CAG GCT     192
Phe Ser Arg Ser Phe Leu Ala Trp Tyr Gln Gln Lys Pro Gly Gln Ala
        50                  55                  60

CCC AGC CTC CTC ATC TAT GGT GCA TCC ACC AGG GCT ACT GGC ATC CCA     240
Pro Ser Leu Leu Ile Tyr Gly Ala Ser Thr Arg Ala Thr Gly Ile Pro
65                  70                  75                  80

GAC AGG TTC AGT GGC AGT GGG TCT GGG ACA GAC TTC ATT CTC ACC ATC     288
Asp Arg Phe Ser Gly Ser Gly Ser Gly Thr Asp Phe Ile Leu Thr Ile
                85                  90                  95

AGC AGA CTG GAG CCT GAA GAT TTT GCA GTG TAT TAC TGT CAG CAG TAT     336
Ser Arg Leu Glu Pro Glu Asp Phe Ala Val Tyr Tyr Cys Gln Gln Tyr
                100                 105                 110

GGT AGC TCA GCT CGG TAC ACT TTT GGC CAG GGG ACC AAG CTG GAG ATC     384
Gly Ser Ser Ala Arg Tyr Thr Phe Gly Gln Gly Thr Lys Leu Glu Ile
            115                 120                 125

AAA CGA ACT GTG GCT GCA                                              402
Lys Arg Thr Val Ala Ala
            130
```

( 2 ) INFORMATION FOR SEQ ID NO:4:

( i ) SEQUENCE CHARACTERISTICS:
    ( A ) LENGTH: 134 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Phe Ser Arg Ser Phe Leu Ala Trp Tyr Gln Gln Lys Pro Gly Gln Ala
        50                  55                  60

Pro Ser Leu Leu Ile Tyr Gly Ala Ser Thr Arg Ala Thr Gly Ile Pro
65                  70                  75                  80

Asp Arg Phe Ser Gly Ser Gly Ser Gly Thr Asp Phe Ile Leu Thr Ile
```

```
                     8 5                      9 0                       9 5
Ser  Arg  Leu  Glu  Pro  Glu  Asp  Phe  Ala  Val  Tyr  Tyr  Cys  Gln  Gln  Tyr
               100                      105                     110

Gly  Ser  Ser  Ala  Arg  Tyr  Thr  Phe  Gly  Gln  Gly  Thr  Lys  Leu  Glu  Ile
               115                      120                     125

Lys  Arg  Thr  Val  Ala  Ala
         130
```